United States Patent [19]
Doiron et al.

[11] Patent Number: 5,698,866
[45] Date of Patent: Dec. 16, 1997

[54] UNIFORM ILLUMINATOR FOR PHOTOTHERAPY

[75] Inventors: Daniel R. Doiron, Santa Ynez; Gregory S. Graham, Ventura; John Brian Dunn, Buellton; A. Charles Lytle, Nipomo; Brian K. Dalton, Santa Barbara, all of Calif.

[73] Assignee: PDT Systems, Inc., Santa Barbara, Calif.

[21] Appl. No.: 654,059

[22] Filed: May 28, 1996

Related U.S. Application Data

[63] Continuation-in-part of Ser. No. 308,278, Sep. 19, 1994, abandoned.
[51] Int. Cl.$^6$ .............. H01L 33/00; H01L 23/34; H02B 1/00; A61N 1/30
[52] U.S. Cl. .............. 257/99; 257/98; 257/91; 257/88; 257/95; 257/717; 361/676; 361/688; 604/19; 604/20
[58] Field of Search .............. 257/98, 91, 99, 257/88, 432, 95, 717; 250/504 H, 504 R; 361/676, 688

[56] References Cited

U.S. PATENT DOCUMENTS

| | | | |
|---|---|---|---|
| 3,512,027 | 5/1970 | Kupsky | 257/98 |
| 3,950,844 | 4/1976 | Wisbey | 257/88 |
| 4,165,474 | 8/1979 | Myers | 257/88 |
| 4,599,908 | 7/1986 | Sheridan et al. | 250/231 R |
| 4,716,296 | 12/1987 | Baussiere | 250/504 H |
| 5,177,593 | 1/1993 | Abe | 257/88 |
| 5,278,432 | 1/1994 | Ignatius et al. | 257/88 |

FOREIGN PATENT DOCUMENTS

| | | | |
|---|---|---|---|
| 55-140281 | 11/1980 | Japan | 257/98 |
| 62-119987 | 6/1987 | Japan | 257/98 |

OTHER PUBLICATIONS

A Multi-LED Source for Photoradiation Therapy Plenum Press, N.Y. pp. 301-308 (1984) G.

Primary Examiner—Mahshid D. Saadat
Assistant Examiner—Jhihan B. Clark
Attorney, Agent, or Firm—Michael G. Petit

[57] ABSTRACT

A light delivery device including an interchangeable handpiece and a semiconductor light source module adapted to releasably attach to the handpiece. The light source module includes a two-dimensional array of light emitting diodes (LED's) disposed on a surface of a fluid-cooled electrically conductive support plate. The device is adapted for uniformly illuminating a tissue surface with phototherapeutic light. The phototherapeutic light is produced by an array of over-driven LED's mounted on the surface of the heat-sinked support. The semiconductor light source employs a multi-layer construction wherein electrically conductive layers are thermally isolated from each other. The device is rugged, inexpensive and can produce high optical power while operating at a temperature well below the temperature at which device failure occurs. The light source module is adapted to be releasably connected to an interchangeable LED handpiece which provides power to the LED's and conducts a coolant fluid. The light source includes an integral unitary reflector for directing the light output from the individual LED's in the LED array in a desired direction. The reflector is a thin perforated sheet having a top, tissue facing surface and bottom surface and an array of cup shaped openings therebetween, each such perforation in the sheet being disposed to overly a LED in the LED array. The inner surface of each cup-shaped opening has a parabolic vertical cross section and is reflectively coated to maximize red reflectivity.

6 Claims, 6 Drawing Sheets

UNIFORM ILLUMINATOR FOR PHOTOTHERAPY

CROSS REFERENCE TO RELATED APPLICATIONS

This is a continuation-in-part of application Ser. No. 08/308,278; filed Sep. 19, 1994, abandoned.

BACKGROUND OF THE INVENTION

1. Field of the Invention

A semiconductor device for delivering phototherapeutic light to uniformly illuminate a tissue surface.

2. Prior Art

Phototherapy is useful for the transcutaneous treatment of a variety of conditions such as psoriasis and hyperbilirubinemia. Photodynamic Therapy (PDT), a particular form of Phototherapy, has been shown to be an effective method for treating tumors. Photodynamic therapy is presently undergoing extensive basic pro-clinical and clinical testing and development both domestically and internationally. The general method of performing PDT is now well known and described, for example, in U.S. Pat. Nos. 4,968,715; 4,932,934; and 5,028,621 to Dougherty, et al.; and 5,002,962 to Pandey, et al. PDT has also been proposed for the treatment of cardiovascular disease and for the treatment of non-malignant hyperproliferative diseases. PDT involves the introduction of a photosensitizer such as photosensitive molecules (PS) into target tissue, followed by illumination of the photosensitive molecules in situ to destroy or alter the target tissue. The delivery of treatment light from a light source such as a laser or arc lamp to a PS-bearing target tissue commonly employs a fiber optic delivery system with special lensing and/or light-diffusing tips.

Prior to performing PDT a PS such as a hematoporphyrin derivative or tin etiopurpurin is introduced into and retained by hyperproliferating cells in diseased tissue such as cancerous tissue and atheromas. Following exposure of the PS to suitable wavelengths of light the photochemical reaction of the PS can lead to selective destruction of PS-associated cells or tissue. PDT also holds potential for a number of possible applications other than cancer treatment such as for treating microvascular lesions and blood purging. To obtain the desired therapeutic response, PDT requires the in vivo delivery of sufficient activating light to the photosensitizer (PS) within the target tissue. The wavelength of the activating light must be within the absorption spectrum of the PS in order to initiate the photochemical reaction. Secondly, the wavelength of the activating light must penetrate the host tissue to permit initiation and progression of the therapeutic reaction at the desired tissue depth. Additionally, the light must be able to be delivered to the treatment area in sufficient quantities to allow treatment on a reasonable and effective time scale.

Prior art sources of illumination for subcutaneous target tissue undergoing PDT have been primarily lasers. The reasons for this are the efficient deliverability of the laser light through flexible single optical fibers, the single wavelength nature of the laser, the tunability of certain lasers, and the ability to deliver phototherapeutic treatment light at a power level sufficient to permit reasonable treatment times. The combination of these properties has enabled PDT to be administered endoscopically, using the interstitial delivery of the light for the treatment of large, thick or otherwise inaccessible lesions. The disadvantages of using a laser include high cost, large size, complex operating procedures and constant attention to the safety issues required when dealing with laser light.

There are a significant number of diagnostic and therapeutic applications for PDT which do not require either the use of a laser light source or the delivery of light through invasive waveguides. In fact, the majority of the basic pre-clinical and original trials of PDT using hematoporphyrin derivative were performed using non-laser light sources. For example, many cutaneous and subcutaneous skin lesions less than 1.0 cm thick can be treated using non-laser light sources. Skin cancer incidence in the United States of America is over 550,000 new cases per year and rising. Even though a majority of these cases can be easily treated with local resection or other methods, there are a significant number involving multiple and/or recurrent lesions that could be more conveniently treated using PDT. The requirement of using a laser for a light source would limit the clinical use of PDT in many cases due to the high cost and unavailability of a suitable laser. There is a continuing need for a low cost non-laser light source for use in PDT.

There are a number of non-laser light sources that could potentially be used for illumination in certain PDT applications. The properties of such light sources which are required for tissue illumination in PDT are: a) suitable output spectrum; b) brightness or intensity at a suitable wavelength; c) deliverability of light to tissue; d) size; and e) cost. Such non-laser light sources include arc lamps, incandescent lamps, fluorescent lamps, laser diodes and light emitting diodes (LED's). The lamp sources generally have a broad emission spectrum ranging from ultraviolet to infrared. These broad spectrum sources require the use of optical filtering to remove undesired wavelengths from the treatment light, particularly the ultraviolet and infrared, in order to reduce carcinogenic effects and heating respectively. In addition, the low power output of these light sources at suitable phototherapeutic wavelengths and their high divergence, compared to lasers, renders them relatively poor candidates for transmitting sufficient power to diseased tissue by conduction through a small (less than 600 micron core), flexible optical waveguide to effect PDT. The brightest of these light sources is the arc lamp due to the relatively high intensity and small size of the discharge arc. While such lamp technology shows promise for certain phototherapeutic applications, including PDT, lamps require extensive filtering. In addition, a lamp's requirement for high voltage and the concomitant potential for arc lamp explosion is undesirable in a clinical setting.

Laser diode-based illuminating systems which include a power supply and cooling means are known in the surgical art, but are currently too expensive to enjoy widespread clinical use. Such a laser diode illuminating system is described, the example, Puliafito, et. al., (Arch. of Ophthalmology, Vol. 105, 1987) wherein the authors disclose using laser diodes for endophotocoagulation of the retina.

Light emitting diodes (LED's) have also been employed as a light source for phototherapy. LED's have the advantage of small size, typically 0.3 mm by 0.3 mm, narrow emission spectrum bandwidth, typically 20 nm to 40 nm, high efficiency and low cost. There are, however, significant differences between LED's and laser diodes. A light emitting diode (LED) is a solid state electronic semiconductor device capable of emitting light when an electric current is passed through a semiconductor junction within the device. LED-derived light is relatively broad band (20–40 nm) in comparison to a laser diode, has a divergent light output and lacks coherence. The light is produced at very low current levels (20 ma). All of these characteristics of LED's serve to technically differentiate them from laser diodes. The light power emitted by a single LED is relatively low however (approximately 4 milliwatts to 5 milliwatts for the brightest red LED's using the manufacturer-specified driving currents) compared to a laser diode but its emission angle or divergence is low when compared, for example, to the arc lamp so that its actual brightness is reasonably good. The small size of the LED along with its spectral purity and high efficiency suggest that a LED-based light source such as a plurality of LED's disposed in a 2-dimensional array upon the surface of a single support would significantly increase deliverable power density over a large area. The low phototherapeutically effective power output has, however, delayed the acceptance of LED arrays as a suitable light source for PDT because of the long exposure time required to deliver a therapeutic dose of light to a target tissue. While the output intensity of a LED array can be increased by over-driving the LED's in the array, such over-driving results in heat generation of the diode junction which shortens the lifetime of the LED and causes a spectral shift in the light output.

LED's are available in variety of discrete packages as well as several one and two-dimensional array packages. As used herein, an LED array means a 2-dimensional distribution of multiple LED's integrally mounted upon a planar surface of a support. Such an LED array is described, for example, in U.S. Pat. No. 5,278,432 to Ignatius et al. Commercially available arrays, from manufacturers such as Mitsubishi, Hewlett Packard or Stanley Electric, also combine a few LED's in a single package. None of these prior art LED arrays can provide sufficient power density for effective PDT treatments within a practical time interval of less than about 2 hours, nor can they be easily configured in the geometries necessary for the wide range of PDT applications requiting surface illumination.

In applications requiring illumination of broad portions of the skin, such as in the treatment of psoriasis or other hyperproliferative diseases of the skin, an array of discrete light sources may be employed to provide the power densities required to effect the therapy during the office visit. Such an array has been described, for example, by Jori, et al. (*Porphyrins in Tumor Therapy*, Plenum Press, N.Y., 301–308 (1984)). Jori, et al. describe the construction of an LED array and its use as a suitable light source for application of PDT to areas of target tissue which contain an exogenous photosensitive agent such as hematoporphyrin or hematoporphyrin derivatives. Jori, et al.'s device lacks means for cooling the LED's. To provide a therapeutically effective dose of light to a tissue undergoing PDT in a practical intraoperative time of an hour or less, the LED's must be overdriven and loss of treatment light minimized. Overdriving causes the LED's to get hot, which, in turn, causes the center wavelength of the light emission spectral band to change, thereby effecting the absorption efficiency of light by the photosensitizer molecules in the tissue and hence the dosimetry and effectiveness of treatment. Moreover, much of the treatment light emanating from the LED array is reflected or scattered by the target tissue and is lost to free space rendering the actual intensity of phototherapeutic light within the target tissue substantially less than the light incident on the surface therapy.

Lison and Mendes, in UK Patent GB 2212010, issued Nov. 4, 1987, describe a radiation therapy apparatus employing an LED matrix. The patent describes the use of an array of LED's for irradiating tissue. In one embodiment, the LED's are mounted on a contoured circuit board to provide a means for focusing the cumulative light energy from the individual LED's upon a particular target. The device has the same limitations regarding efficiency as the previously described LED array of Jori, et al.

The present invention teaches how to make an efficient light source embodying the characteristics of the LED and adapted for certain applications of PDT not requiring interstitial or endoscopic light delivery. The present invention is a light source for PDT which takes advantage of the wide output distribution pattern, small size, and manageable cooling requirements of the LED to create a device including a large array of the LED's which cumulatively are capable of producing a total output light power exceeding that of laser diodes. This opens up applications for large surface area illumination (such as is needed in dermatology) for which laser diode systems are inadequate.

SUMMARY OF THE INVENTION

It is an object of this invention to provide an illuminating device employing an array of multiple integrated LED's operable for delivering light to a tissue which light is useful for photodynamic therapy.

It is another object of the invention to provide an efficient, inexpensive light source useful for photodynamic therapy.

It is still another object of this invention to provide an LED array-based light source for photodynamic therapy that is capable of uniformly illuminating the surface of various types of tissues.

It is yet a further object of this invention to provide an LED array for photodynamic therapy which enables accurate wavelength and exposure control and permits accurate dosimetry.

It is another object of this invention to provide an illuminating system for photodynamic therapy that is safe to both the physician and the patient.

It is an object of this invention to provide a efficient light delivery device for phototherapy which includes a reflector adapted for use with an array of multiple integrated LED's disposed upon a surface which reflector enhances the intensity of therapeutically effective light delivered to a target by the LED array.

It is another object of the invention to provide a high power light source for phototherapy of tissue surfaces.

These and other objects of the invention will soon become apparent as we turn now to a brief description of the drawings.

BRIEF DESCRIPTION OF THE DRAWINGS

FIG. 21(a) shows back-scattered or reflected treatment light re-reflected into the target tissue by the reflector portions of the LED light source in accordance with a preferred embodiment of the present invention. (b) shows a portion of the treatment light incident upon the target tissue being reflected or back-scattered and lost to free space in the absence of a reflector on the light source.

DESCRIPTION OF THE PREFERRED EMBODIMENT

As discussed above, it is the combination of small size and high efficiency that make the LED a potentially useful light source for phototherapy and particularly for PDT. The small size of the LED allows these semiconductor light sources to be fabricated in high density upon light delivery devices of various shapes for the direct contact treatment of cutaneous lesions. The device shape may be circular, rectangular (or affixed any curvilinear surface) for treating skin lesions or to a cylindrical surface for the treatment of cervical cancer. Planar arrays of LED's may be bent or folded to form various curvilinear surfaces to conform to the surface being treated. To be useful, LED's which are currently available and have operating specifications in accordance with the state of the art, must be overdriven to produce useful therapeutic power outputs and practical treatment times. The heat generated during over-driving must be removed by cooling the LED in order to control the wavelength and increase the lifetime of the LED. In addition, a practical device suitable as a light source for surface illumination during phototherapy must be made more efficient to further reduce treatment time.

Figure 1:
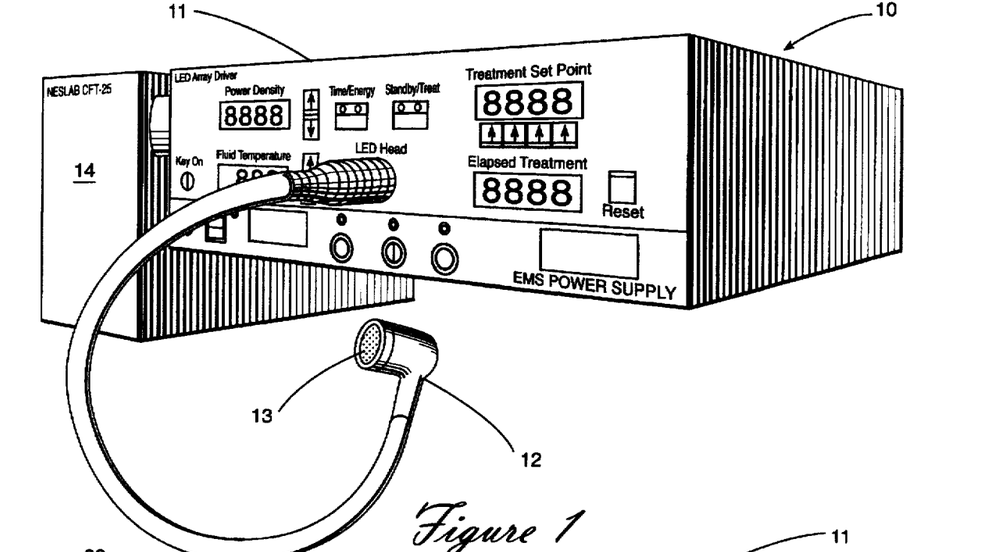
FIG. 1 is a schematic representation of an LED system suitable for illumination surfaces for photodynamic therapy.
Figure 2:
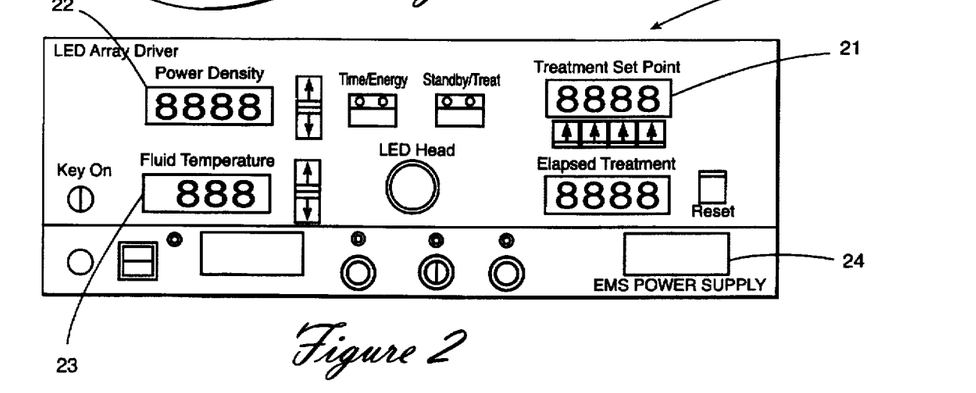
FIG. 2 schematic diagram of the front panel of the LED array driver showing the displays for controls for exposure power and coolant temperature display.

Turning now to FIG. 1, a schematic view of the LED-based light delivery system configured for flat surface illumination is generally indicated at the numeral 10. The system 10 consists of the LED array driver 11, the hand piece 12, the planar LED array light source 13 and a closed loop fluid circulating heat exchanger 14. The controls for operating the light delivery system are presented on the front panel of the LED array driver housing 11 shown in FIG. 2. The front panel includes the controls and displays for exposure 21, power 22, the coolant temperature display 23 and the power supply 24.

Figure 3:
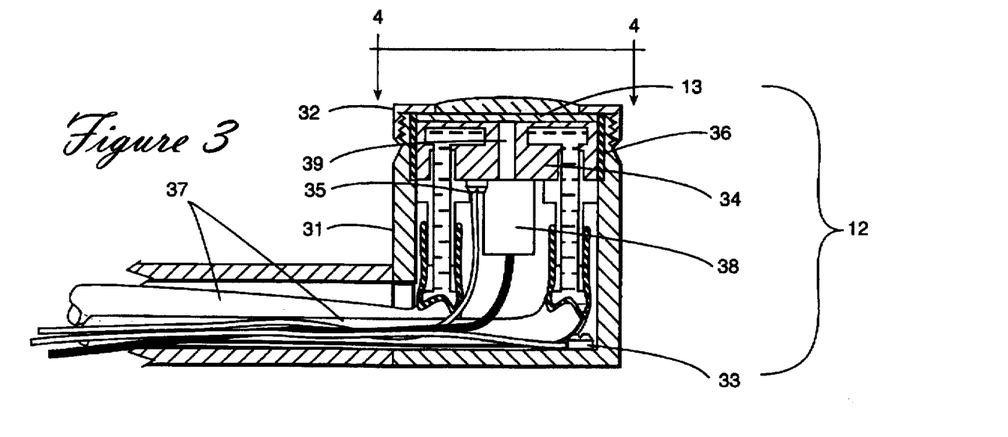
FIG. 3 is a cross-sectional elevational view of the LED hand piece configured for flat surface illumination.

An LED handpiece 12 housing a LED light source 13 configured for flat surface illumination is shown in vertical cross section in FIG. 3. The stainless steel housing 31 and threaded LED light source retaining ring 32 are connected to the system ground 33 and provide electrical connection between the anode (positive) of the LED supply voltage and the anode of each LED in the LED array within the light source 13. The heat sinked support 34 is connected to the LED supply voltage 35 providing the second electrical connection to the LED's comprising the light source as well as removing heat generated by the LED's mounted on the support. The heat sinked support 34 is electrically insulated from the housing by a DELKIN® insulator 36. The coolant tubes 37 provide a circulating flow of cooling water between a chiller 14 and the heat sinked LED support 34. The output power and wavelength of the therapeutic light delivered to the patient are monitored by sampling and conducting a portion of the light through a light sense channel 39 to a detector 38 (shown in greater detail in FIG. 8) which detects the amount of light.

Figures 4, 5, 6:
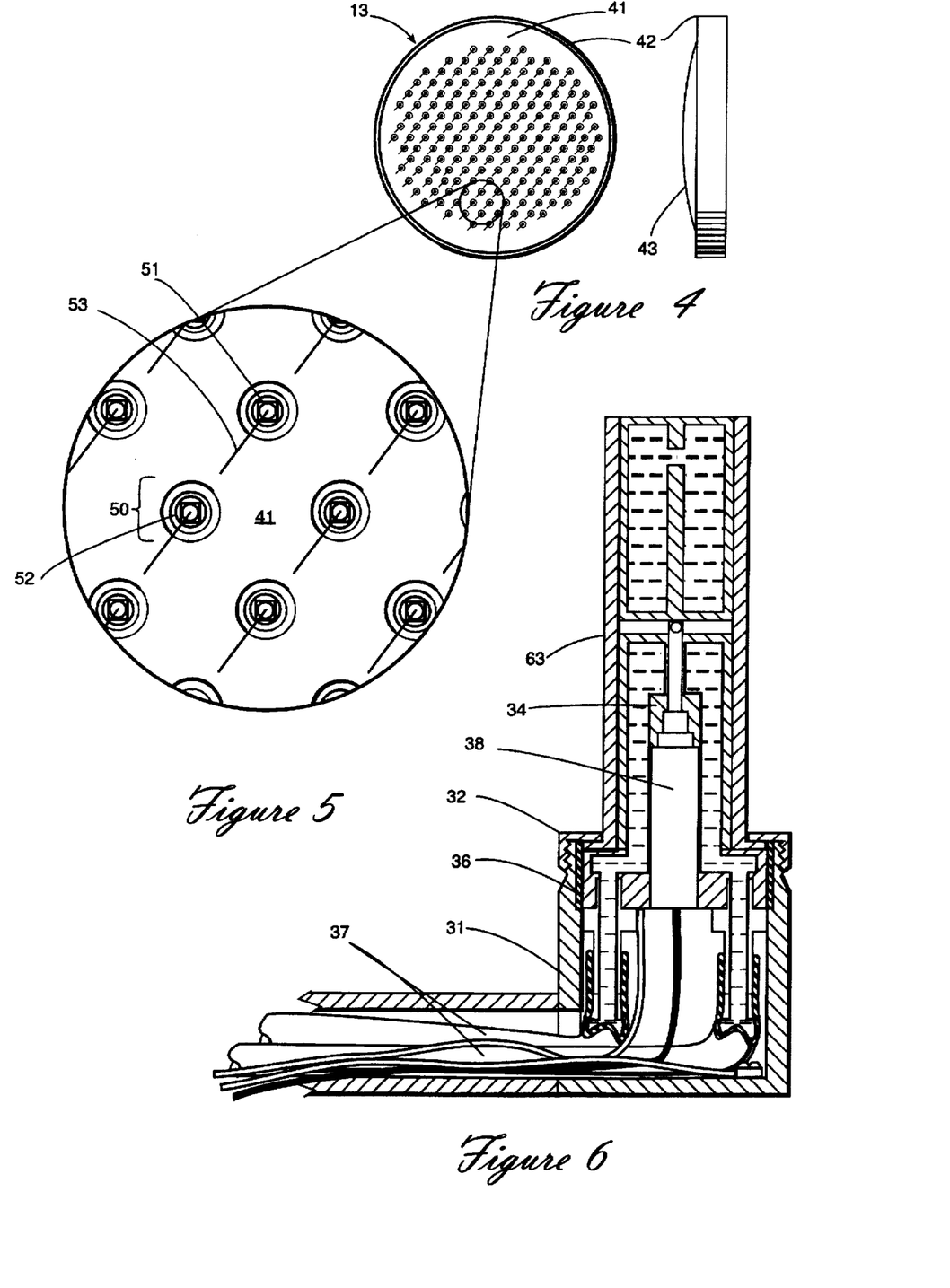
FIG. 4 is a top view of the LED light source configured for flat surface illumination.
FIG. 5, which is a detailed top view of the area shown in FIG. 4 enlarged for ease of viewing, shows the top surface of the LED light source showing the machine holes and indicating the LED die.
FIG. 6 is an elevational cross-sectional view of an embodiment of the LED handpiece adapted for illumination of cylindrical outer surfaces.

An embodiment of a LED light source configured for flat surface illumination is shown in FIG. 4. The LED light source,, generally indicated at 13, comprises a gold plated insulated copper and fiberglass laminate sheet 41 bonded to a surface of a copper support substrate 42 Holes 50 (see FIG. 5, Detail A) are machined through the copper laminate sheet 41 to the surface of the copper support substrate. The LED's 51 in the array are mounted within the holes 50 in electrical and thermal contact with the support 42 and coated with a clear epoxy potting material 43 to protect the LED's arranged on the support and provide a smooth clean surface for patient contact.

FIG. 5, shown as detail A of FIG. 4, is an enlarged view of the top surface of the LED light source 13 showing the LED's 51 bonded to the copper support substrate 42 with an electrically and thermally conductive epoxy adhesive 52. FIG. 5 also shows gold bonding wire 53 connecting the top electrical contact of the LED with the electrically conductive upper surface of the copper laminate 41 using common integrated circuit assembly techniques.

FIG. 6 shows a cross sectional view of an LED handpiece and LED light source 63 adapted for illumination of the outer cylindrical surface of a tissue. The stainless steel housing 31, threaded retaining ring 32, coolant tubes 37, the photodiode detector 38 and the insulator 36 function the same as in the flat surface illuminating handpiece 12. The handpiece and light source are shaped for insertion into the cervical canal or rectum.

Figure 7:
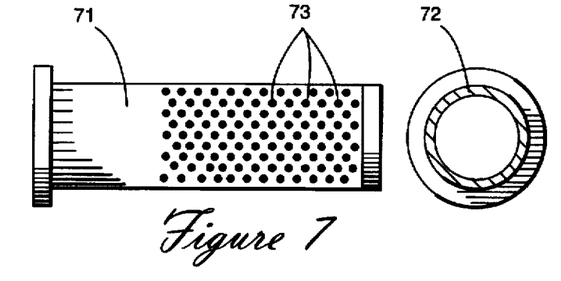
FIG. 7 shows an embodiment of the LED light source adapted for cylindrical inner surface illumination.

FIG. 7 shows an LED light source and handpiece configured for cylindrical surface illumination 63. The copper laminate 71, copper substrate 72 and LED array 73 mounted on the support 72 are assembled in a similar manner to the flat surface LED light source except the LED array presents a cylindrical surface.

Figure 8:
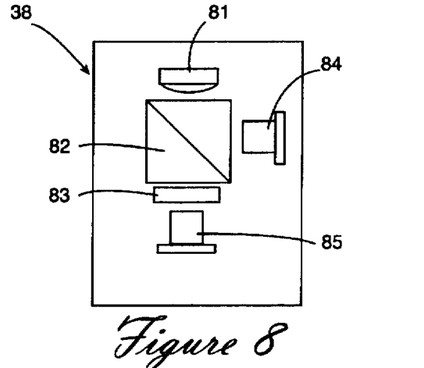
FIG. 8 is a schematic diagram of a preferred embodiment of a light source output monitor and wavelength detector.

The light output power and wavelength detector for measuring the light emanating from the light source is shown in greater detail in FIG. 8. A portion of treatment light transmitted through the light sense channel 39 (FIG. 3) is focused by a collimating lens 81 and split into two equal light beams by a beamsplitter 82. The light in one beam path passes through a filter 83, and the filtered transmitted light measured by the photodiode 85. The photodiode 84 measures the unfiltered light power in the other light beam path. After calibration to compensate for the different light losses attributed to interactive optical elements in each beam path, the total optical power being delivered by the light source and verification of the wavelength can be monitored. It is clear that the light source could also be configured with a flexible light guide (not shown) built into the handpiece which would then deliver the sampled portion of the LED derived treatment light to a light power output and wavelength detector shown in FIG. 8 which could conveniently be installed in the LED array driver 11.

Figure 9:
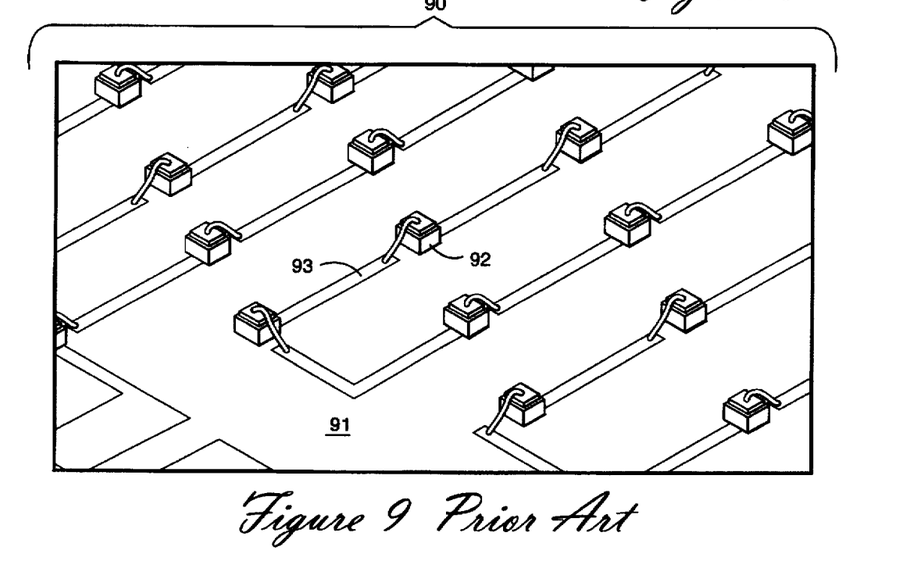
FIG. 9 is a perspective view of an LED array in accordance with the prior art.
Figure 10:
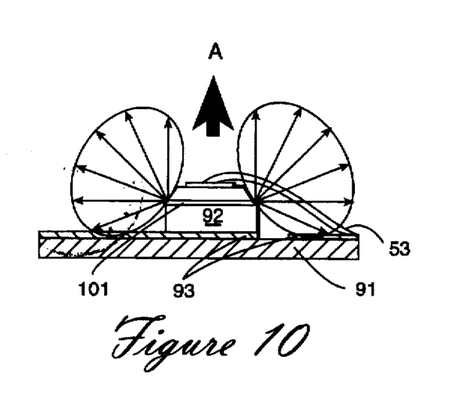
FIG. 10 is an elevational view of an LED showing the light output distribution pattern for a LED configured for flat surface illumination.

The LED light source includes a reflector which is operable for increasing the portion of LED derived treatment light which penetrates the target tissue. The reflector redirects treatment light reflected by the target tissue back to the target tissue thereby increasing the efficiency of the LED light source. This allows the LED array light source to be operated at reduced power levels and/or for a reduced time thereby reducing the amount of overdriving the LED's cooling and increasing the lifetime of the LED's in the array. FIG. 9 shows a schematic view of an LED array in accordance with the prior art. The prior art LED light source 90 is configured for flat surface illumination. A support substrate 91 has a plurality of LED's 92 mounted thereon. The LED's 92 are in electrically connected to a power source (not shown) by means of conductive strips 93 affixed to the substrate. The LED's 92 are arranged in series on the conductive strips 93 which strips are, in turn, connected in parallel to a power source. Thus, if a single LED in the series of connected LED's fails, the LED's connected thereto fail. The output light intensity distribution from an individual LED 92 in the array 90 is indicated in FIG. 10 in which the LED 92 is seen in cross section. The light, indicated by the plurality of light arrows, emanates from the semiconductor junction 101 within the LED 92 and is distributed spatially as shown. The majority of the emitted light must be redirected in the direction of heavy arrow A to impinge upon the target tissue being irradiated.

Figure 11:
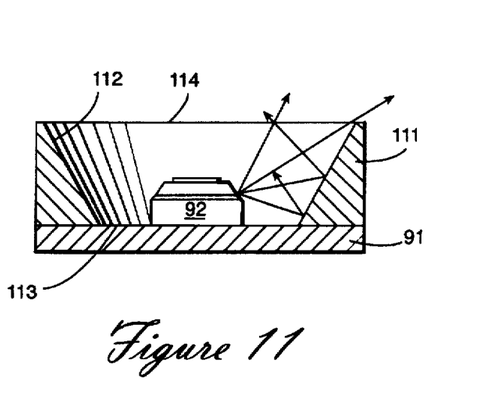
FIG. 11 is a cross sectional elevational view of possible light paths for light from a single LED surrounded by a tapered reflective surface shaped like the frustum of a cone.
Figure 12:
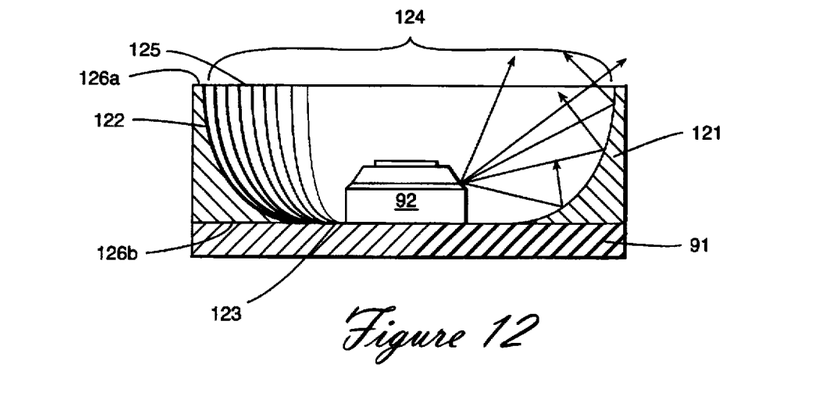
FIG. 12 is a cross-sectional elevational view of the light paths from an LED surrounded by a parabolic reflector shape in accordance with the present invention.

Two possible solutions to the problem of redirecting the light from the LED junction in a preferred direction is shown in FIGS. 11 and 12. FIG. 11 shows a LED light source including a reflector device 111 comprising a solid substrate with a conical hole cut therein. The hole has a large opening 114 in the upper surface of the reflector and a small opening 113 in the lower surface which is bonded to the substrate 91 supporting the LED's 92. The small opening 113 surrounds and is centered upon the LED 92 mounted on the support substrate 91. The outer or tissue-facing surface of the reflector device 111 is perforated with openings shaped like cups and having an inner surface 112 which receives light emanating from the LED 92 and which is preferably coated with a highly reflective material.

FIG. 12 shows a preferred embodiment of the reflector device of the present invention in which the cup-shaped perforation in which the LED 92 is centered in top plan view is parabolic in vertical cross-section. The reflector 121 portion of the LED light source comprises a sheet having an upper surface and a lower surface which is bonded to the LED support substrate 91 by means of an appropriate non-electrically conductive adhesive. The small circular hole 123 at the base of the cup (i.e., in the lower surface of the reflector and adjacent to the LED support 91) surrounds the LED. The large hole 124 at the upper surface of the reflector 121, provides an aperture for light from the LED junction to exit the light source. The inner wall 122 of the cup-shaped perforation is directly exposed to light emanating from the LED and is preferably coated with a highly reflective material such as gold or silver.

Figure 13:
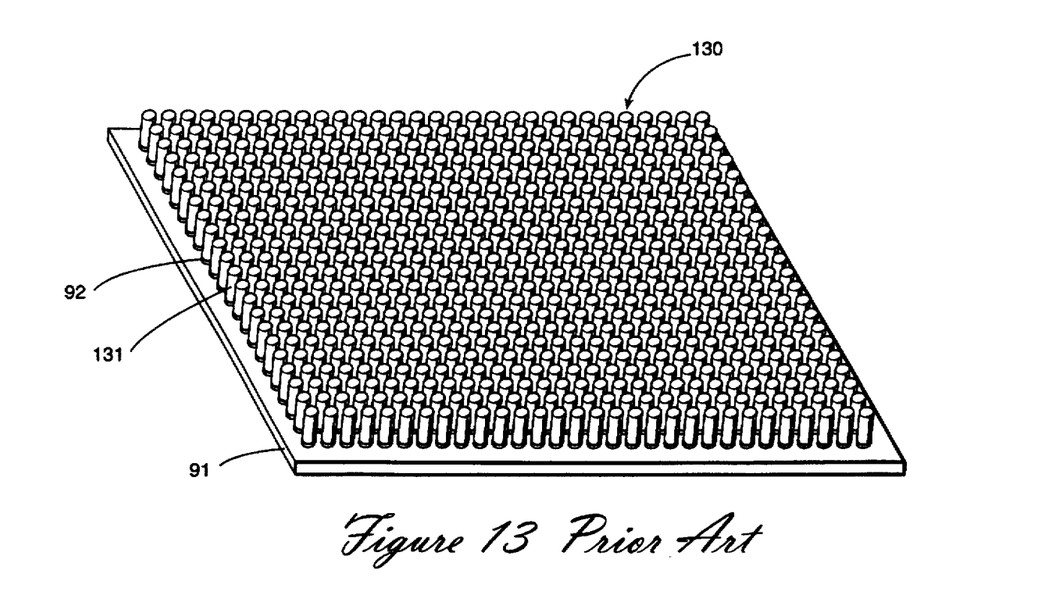
FIG. 13 is a perspective view of a prior art LED array employing lenses over the individual LED's to redirect the emitted light.

Prior art LED arrays employ lenses for redirecting and focusing light emanating from the individual LED's as shown in FIG. 13. The prior art LED light source 130 comprises an array of individual LED's 92 distributed on a support substrate 91 with lenses 131 affixed thereto to redirect the light in a preferred direction normal to the plane of the LED array. The construction uses microlenses to focus the light from the LED's. The microlens increases the size of the LED structure and reduces the density at which LED's may be packed on a support surface. The present invention eliminates the need to embed the LED's in a lens by providing a reflector as shown at 121 in FIG. 14 wherein perforations are arrayed on the sheet in such a manner that the position of the perforations in the reflector are registered to center upon the LED's (not shown in FIG. 14) of a mating array mounted on a support. The diameter of the small, substantially circular opening 123 of the cup-shaped perforation in the bottom surface 126b of the reflector is dimensioned to be larger than the LED. The opening of the cup-shaped perforation 124 at the top surface 126a of the reflector is also circular and dimensioned to provide the interior surface of the perforation with a vertical profile approaching that of a parabolic cup. The tapered surface approximating the frustum of a cone surrounding each LED as shown in FIG. 11, is not as efficient at redirecting the light in a direction normal to the support surface upon which the LED's are arrayed as is the array of parabolic cups shown in FIG. 12.

Figure 14:
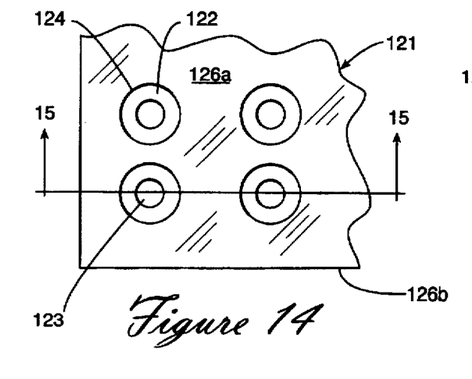
FIG. 14 is a top plan view of a portion of the unitary reflector device of the present invention configured for use with a quartet of discrete LED's which, in turn, are configured for flat surface illumination.

A reflector 121 for improving the efficiency of a LED light source in accordance with the present invention comprises a sheet having a plurality of parabolic perforation therethrough is easily made as follows. Both the top and bottom surfaces of a ½ mm plate 125 are coated with a first layer of a chemically resistant material. The top surface is additionally coated with a patterned second layer of masking material. The chemically resistant coating is then removed from the unmasked portion of the upper surface 126a of the reflector 121 to expose an uncoated pattern on the surface 126a of the reflector 121 comprising small circles centered and disposed to match the LED spacing on an LED array. After a pattern of uncoated circles on the upper surface 126a is thus exposed, the reflector sheet 121 is immersed in an etchant bath and an electrical voltage applied between the bath and the conductive surface of the reflector 121. The chemical action etches the structural conductive material constituting the reflector 121 from the portion of the sheet underlying the exposed pattern on the upper surface. The progression of erosion of material by the etchant acting on all uncoated surface in contact with the both creates a pattern of perforations in the sheet 121 having the desired parabolic shape as the etchant dissolves the reflector material substrate and eventually erodes through the lower surface of the plate to form a smaller diameter circular opening therein. This manufacturing technique, which is known in the art as chemical milling, is inexpensive. The reflector 121 material is preferably a copper sheet 0.5 mm thick. After chemically milling the parabolic perforations into the sheet, a coating of gold applied to the parabolic surface to increase the reflectivity of the surface to reflect around 90 percent of the LED derived light incident thereon. Although pure polished copper presents a highly reflective surface, the copper will oxidize in air and the resultant oxide does not have a efficient reflective surface. Alternatively, the metallic surface of the sheet forming the surface of the perforations can be coated with a number of alternate dielectric reflective coatings or a transparent film which can perform a protective barrier to prevent oxidation of a polished copper surface.

Figure 15:
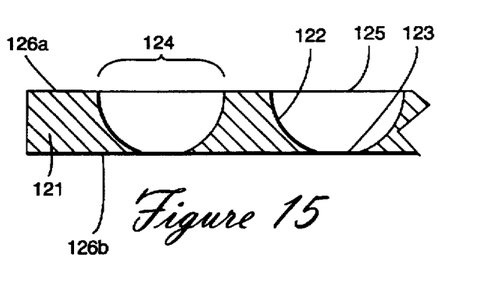
FIG. 15 is a elevational cross-sectional view of the reflector device of the present invention taken along section line 15—15 of FIG. 14.
Figure 16:
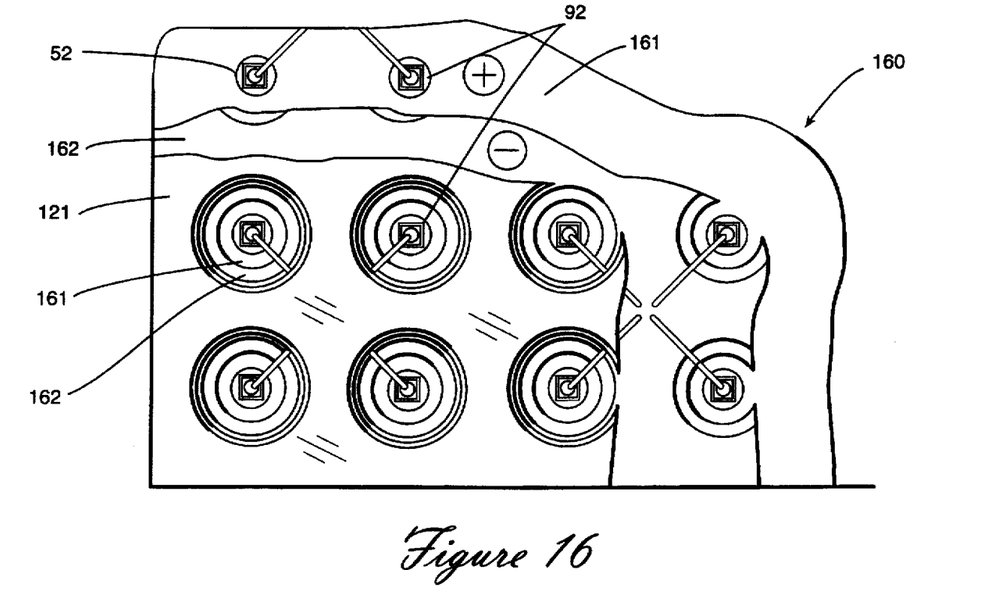
FIG. 16 is a partially cutaway top plan view of a preferred embodiment of a light source in accordance with the present invention with the unitary reflector array positioned over an LED array.

A portion of the reflector suitable for use with a LED array to improve the efficiency of light delivered to a tissue is shown in cross-section in FIG. 15. The diameter of the circular opening 123 in the lower surface 126b of the reflector sheet where the perforation intersects the lower surface is larger than the LED's (not shown), and the spacial distribution of parabolic perforations on the reflector corresponds to the spacial distribution of LED's on the LED array. The diameter of the larger circular opening 125 formed at the intersection of the parabolic perforation 124 and the upper surface 126a of the reflector sheet depends upon the thickness of the reflector sheet and is dimensioned to provide the perforation with a surface exhibiting a parabolic profile in vertical cross-section. FIG. 16, which shows a particularly preferred embodiment of a light source in accordance with the invention and which embodiment will be discussed in more detail below, shows a portion of a reflector in accordance with FIG. 15 mounted on a LED array support and correctly positioned upon the support to provide a parabolic reflector surface around each LED in the array. Each of the reflector perforations are centered on a corresponding LED mounted on the LED support 91.

EXAMPLE

SYSTEM CONSTRUCTION

Figure 17:
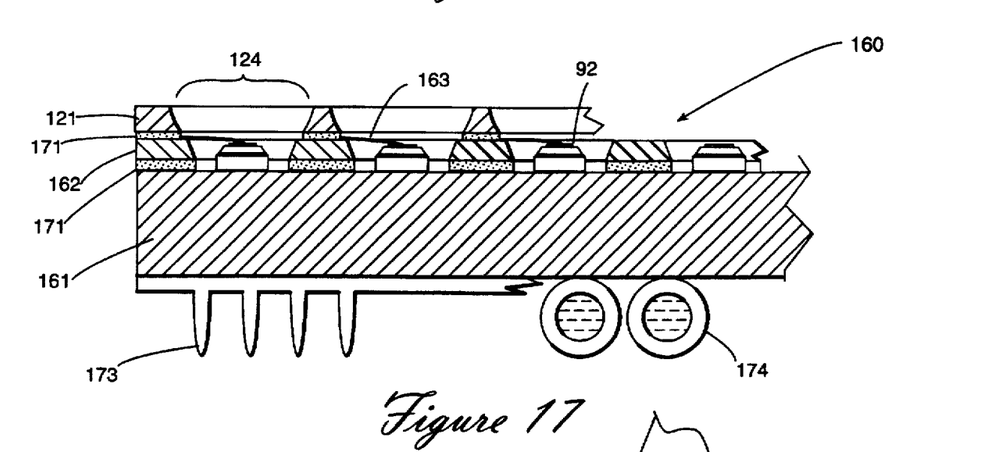
FIG. 17 is a side cross-sectional view of the preferred embodiment of the light source shown in FIG. 16.

FIGS. 16 and 17 show an LED light source 160 adapted to provide light for administering PDT. This LED-based light source 160 delivers therapeutic light to a surface at incident irradiance levels of 100 to 200 mW/cm$^2$ by mounting a plurality of AlGaAs diodes 92 to a heat sinked electrically conductive support 161 in a two-dimensional array at a density of 36 LED's per square centimeter. This high density packing allows the needed irradiance to be produced with reasonable diode drive currents of 25 mA. In addition to high packing density, the unitary reflector 121 affixed to the electrically conductive layer 162 overlying the LED array support 161 by means of a non-electrically conductive adhesive 171, improves efficiency of the light source. the light source 160 provides high irradiance levels at the surface of a target tissue by reflecting light from the LED to the target tissue and by re-reflecting treatment light which is reflected by the surface of the target tissue, redirecting the light toward the target tissue. The embodiment of the light source 160 shown in FIGS. 16 and 17 will be discussed in detail later on.

A handpiece adapted to receive a LED light source and provide electrical power thereto and also means for cooling the LED source. The handpiece includes means for attaching the handpiece to a target tissue. One set of handpieces which are commercially available include a square LED array ranging from 4 cm×4 cm, through 4 cm×8 cm and 8 cm×8 cm arrays (PDT Systems, Inc., Santa Barbara, Calif.) and can be driven by the control unit. LED arrays will generate appreciable heat when driven to deliver the high light power output levels sufficient to meet clinical needs. To control heat build-up in the array, the LED light delivery device incorporates a fluid flow channel within the handpiece and employs liquid cooling to maintain precise temperature of the LED light source attached thereto. Ultimately the thermal load, created by the LED's, is transferred to the atmosphere with air cooling within the system console. A flexible utility cable provides electrical connection between the LED light source and a power supply and flow connection between the handpiece and a coolant fluid source. The cable also provides electrical connection between the photodiode detector in the LED light source and the controller.

Figure 18:
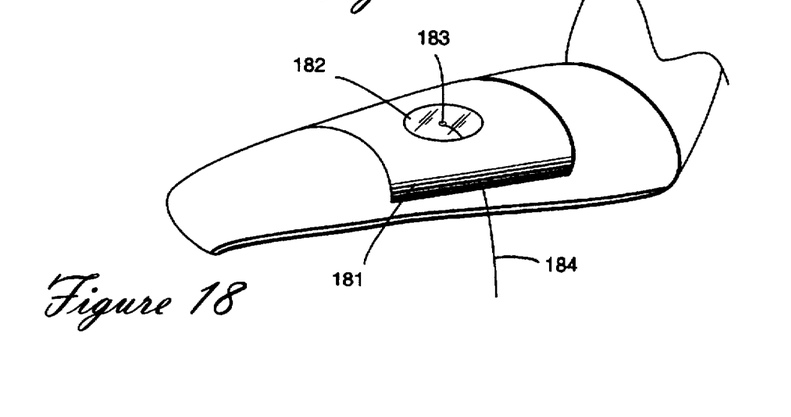
FIG. 18 is a perspective view of a light source measuring device positioned on a persons arm to measure light delivered thereto.

The present LED-based light deliver device preferably includes means for measuring light dose (J/cm$^2$) administered to a target tissue via an isotropic fiberoptic pick up which is placed in contact with the tissue. A fiber optic pick up (PDT Systems, Inc. Model 2818 Isotropic Probe (ISP)) is used in conjunction with a sterile biological shield placed over the lesion comprising the target tissue to isolate it from the non-sterile handpiece as shown in FIG. 18. The shield 181 contains a transparent window 182 overlying the ISP 183. The transparent window 182 allows light from the LED-based light source (not shown in FIG. 18) to reach the underlying target tissue. Irradiance incident upon the ISP 183 is conducted to a microprocessor (not shown in FIG. 18) within the system housing by means of a fiber optic 184 to control the exposure time and the light dosage administered to the tissue.

The microprocessor, power supply and controls for the present light delivery device is housed within an 18 in.×20.5 in.×7 in enclosure shown as 11 (FIGS. 1 and 2) and weighs less than 45 pounds. The handpiece 12, when placed on a patient's skin, produces a pressure of less than one-half pound per cm$^2$ on the supporting tissue. The universal power requirement for the LED light delivery device is either 110V or 240V, at 60 Hz or 50 Hz, with a maximum current draw of 77 Amps. While total system reliability is currently being determined, MTF of the individual LED's in the LED array under the above operating parameters is >10,000 hours.

Figure 19:
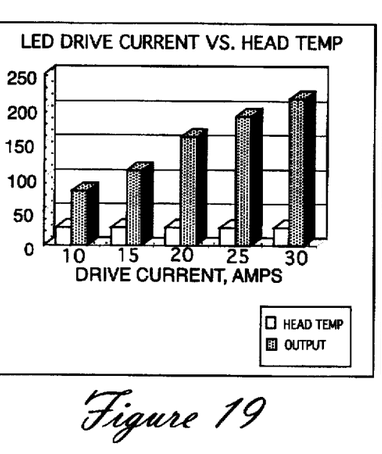
FIG. 19 is a graphical representation showing the LED array temperature with various current and light output.
Figure 20:
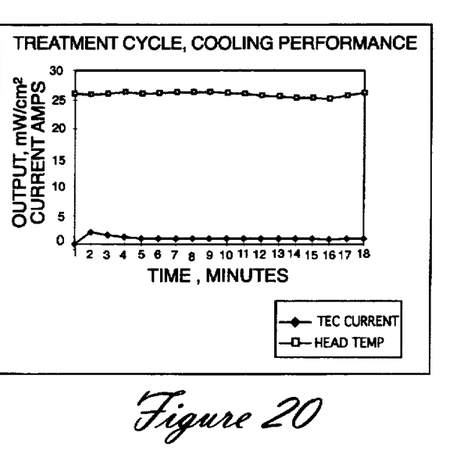
FIG. 20 shows the temperature of the LED array and constant current over a period of time.

Two features are central to the satisfactory performance of the LED light delivery device: sufficient optical power delivery to effect therapy in an hour or less and efficient thermal control of the LED array at the target tissue/LED array interface. In FIG. 19, it is seen that total array drive currents up to 30 Amperes at 1.8 Volts can be delivered while holding the temperature of the array at an acceptable level of 27 degrees Celsius. At the 30 Amp level, the optical irradiance into free space is above 200 mW/cm$^2$. It is important to bear in mind that space irradiance within a target tissue is very different than and much less than space irradiance into free space because target tissue reflects or back-scatters much of the treatment light incident thereon which light is not available for phototherapy. These measurements were made using the 4 cm×4 cm array referenced above. Normally this array size is run at 15 Amps which will create irradiance levels of appropriately 125 mW/cm$^2$ into free space. The present system delivers more than sufficient optical power for PDT and permits the operator to control the temperature adequately while doing so as shown in FIG. 20.

Operation of the LED light delivery device and control system presented herein is easily performed as follows. On initial turn on, the system provides power to the LED light source goes through an automated internal safety check and initializes into a standby mode wherein the system is ready for either a low power visual examination of the LED array-based light source's output (accessible by pressing the TEST button) or for treating the patient. Prior to treatment, the desired light dose is set using the up-down keys under the TARGET display window. Once set, the System is ready to deliver the required optical energy.

Next, the biological shield 180 is placed over the patient's lesion (the "target tissue") and the surrounding tissue adjacent to the lesion is masked for precise exposure of the target tissue. The LED light source and handpiece 12 is then placed over the window 182 of the biological shield 181 and secured by suitable means such as Velcro straps or surgical tape. Once the handpiece supporting the LED array-based light source attached thereto overlies the target tissue the treatment begins by pressing the TREAT button. As treatment commences, the system control unit provides a continuous display of both treatment time remaining and total delivered light (J/cm$^2$).

As mentioned above, a measurement of the amount of light emitted in free space by a LED array (or any other light source) does not accurately indicate the amount of light available for activation of a photosensitive drug within the target tissue. In practice, actual photons available for absorption by the photosensitive (PS) drug can be far different than the dose of photons calculated by using the irradiance measurement at the light source-target tissue distance for the light source in free space. This is due, in great part, to internal reflections and scattering of treatment light occurring within the tissue being treated. These factors represent losses of light which affect dosimetry.

Figure 21:
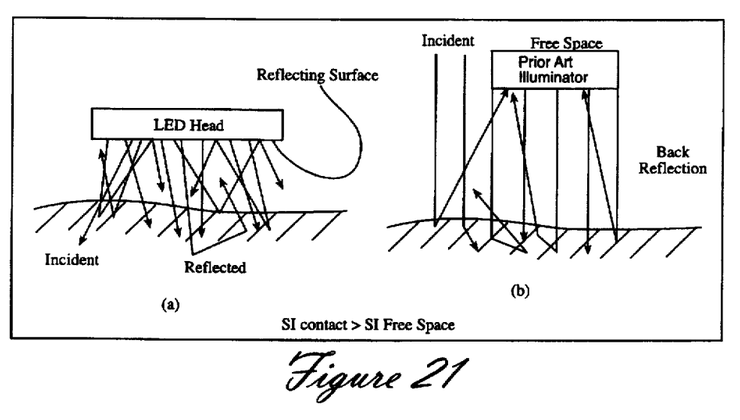
Figure 22:
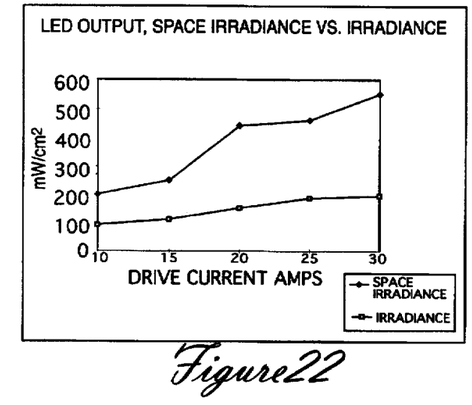
FIG. 22 shows the difference between measured irradiance and actual space irradiance at the target tissue as a function of LED array driving current.

FIG. 21 shows some of the possible paths for rays of treatment light which emanates from a LED light source. The present LED light source emitting rays of treatment light as shown in 21a on the left on FIG. 21, re-reflects the light rays back-scattered or reflected by the tissue surface whereas when a prior art LED light source is used, as shown in 21b, the tissue-reflected light rays are lost to free space. FIG. 22 shows actual radiometric values for incident irradiance in free space and Space Irradiance intensities at the same power level as measured on the arm of one of the present inventors. This dramatic doubling of power realized with the present LED light source is due solely to reduction in loss of treatment light due to tissue reflectivity. The loss of treatment light is reduced with the present device by redirecting the exiting photons back to the target tissue by reflection from the reflector surface of the LED light source. When the required dose of treatment light has been delivered, the system terminates light delivery and goes to the treatment COMPLETE mode where further treatments can be initiated by recycling through the RESET to the STANDBY/TREAT Cycle.

Thus, as shown in FIG. 22, re-reflection of this reflected treatment right by the reflector portion of the LED array-based light source generates Space Irradiance levels 2.5 times greater than the incident irradiance. In laser light application using a microlens, the Space Irradiance as compared to the incident irradiance levels are in the area of 1.2 to 1.5 times higher, differing due to tissue variations.

EXAMPLE 2

SYSTEM PERFORMANCE

Establishing a standardized LED/Laser equivalence for dosimetry in biological systems is central to the continued development of the present LED light source technology for PDT. To establish a phototherapeutic dosage equivalency between light sources a biological model consisting of a C3H Mouse having a BA Mammary Carcinoma implanted subcutaneously was employed. The criteria for a cure was that there was no reoccurrence of the tumor at 40 days The photsensitizer utilized in this evaluation was Tin Ethyl Etiopurpurin (SnET2) administered I.V. into the mouse tail vein 24 hours prior to initiating treatment irradiance.

The control laser light source used was a dye laser (600 Series Dye Module, Laserscope, San Jose, Calif.). This dye laser is used in conjunction with a Laserscope 660 Nd/KTP Surgical Laser. This combination of laser light sources emits a 660 nm beam of treatment light with a FWHM of less than 3 nm and to date has been the standard light source employed for clinical trials. Using SnET2, the present system using LED array light source was compared to this control to establish the effect on dosimetry required for a cure in view of the 25 nm band width of the LED array source and the 665 nm emission peak and contact with target tissue in use.

Figure 23:
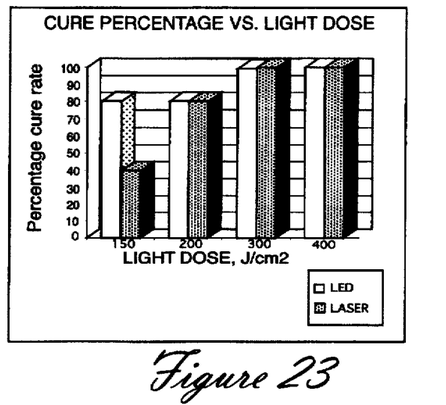
FIG. 23 shows the substantial equivalence between laser light source space irradiance and LED array light source space irradiance due to the incorporation of a reflective surface in the light source.

The intensity of both sources were adjusted to produce a measured space irradiance of 110 mW/cm$^2$ on the tumor surface. The resultant data can be seen in FIG. 23 showing near complete functional equivalence. The slightly higher performance of the LED at 150 J/cm$^2$ is thought to be due to a function of biological variability rather than an increased efficacy of the LED.

CONSTRUCTION OF THE PREFERRED EMBODIMENT

A particularly preferred embodiment of a LED array-based light source adapted to provide uniform illumination to the surface of a target tissue and meeting the requirements for the practical administration of PDT is shown in FIGS. 16 and 17. The LED's 92 are mounted upon a thin, solid copper plate (1.5 mm), nickel flashed, gold plated with conventional conductive silver epoxy. This plate 161 which is referred to as the support substrate, or alternatively as the "anode" or "support" or "support plate," is the positive electrical contact, or the positive buss for providing power to the LED's.

A second layer of thin, perforated sheet of copper 162 which is nickel flashed and gold plated is glued over the support substrate 161. The thickness of the second layer of copper sheet 162 is equal to or greater than the thickness of the LED's so that the upper surface of the sheet 162 if higher than the top of the LED's. The sheet 162 has peripheral electrically conductive attachment means on the surface thereof. One conductive lead on each LED is connected to the electrically conductive surface of sheet 162. Since each perforation in the sheet 162 is centered on a LED. The sheet 162 does not interfere with the positioning or operation of the LED's. The gold plating is highly reflective in the operating wavelengths, but alternate coating materials can be used to provide high reflectivity at the wavelengths used. The thickness of sheet 162 can be modified with consideration given to the electrical current supply requirements of the particular application. This second layer of copper sheet 162 will be referred to as the negative plate, or as the cathode, which is the negative electrical contact, or negative buss to which the cathode of the LED's is connected.

Negative plate 162 is perforated with a plurality of conical holes. Each hole is circular when viewed from the top and centered upon each LED mounted to the support substrate 161. The conical hole has a diameter approximately 3 times the diameter of the centrally located LED. The hole is etched by chemical milling techniques as described earlier to give a smooth parabolic or conical contour to the wall of the hole. Sheet 162 supplies electrical power the LED's and must have low resistance and the capability of carrying high levels of electrical current. If the ohmic resistance of a current path for a particular LED in the LED array is different than the resistance in the current path for other LED's in the array, a non-linear variation in space irradiance results. Since the thickness of the cathode 162 is substantially greater than the thickness of conductive traces of a conventional printed circuit board, a substantial gain is made in the current carrying capability of the device, providing equal current to each LED which produces a more uniform light output tom the device.

There is an advantage to keeping the spacing between anodic and cathodic layers of copper sheeting 161 and 162 as small as possible. LED's have an optical power output pattern that is toroidal Lambertian, having a wide dispersion angle. Although the conical reflective wall of the holes between the lower and upper surfaces of the negative plate 162 redirect the portion of the LED 92 output light incident thereon upwardly, the adhesive space between the anode 161 and the negative plate 162 collect a portion of the light radiated from the LED's and present a potential loss of power efficiency. The electrically insulating adhesive 171 between layers 161 and 162 is applied in multiple, small, spot pattern, spaced evenly upon the surfaces to be bonded. Although the adhesive pattern is spaced closely, the area of the uncoated surface is large in comparison to the coated area. This allows light which has entered the space between parallel adjacent surfaces on sheets 161 and 162 to continue reflecting between the gold plated surfaces until the light enters an adjacent perforation where the light encounters a reflective surface and is directed out of the device. Thus, there is less heating of the LED light source by light absorption and more power produced by the array.

The adhesive 171 which bonds the two electrically conducting sheets 161 and 162 together provides an electrically insulative spacing between the two opposite electrically charged surfaces. The electrically insulative adhesive 171 is preferably a non-conductive epoxy which is first deposited on the copper surface of the support substrate 161 by printing means such as a stencil, silk-screening or contact transfer. After applying the adhesive pattern to the upper surface of the support 161, the wet adhesive pattern is cured. A complementary pattern of adhesive is applied to the bottom surface of the negative plate 162 the adhesive deposits disposed to overlie and mate with the cured adhesive deposits previously printed on sheet 161. The support substrate 161 and the negative plate 162 are then brought together under moderate fixturing pressure to insure the proper positioning of the components. The adhesive is allowed to cure, and the laminate consistency of 2 parallel sheets affixed to each other is removed from the fixturing. This construction technique creates a strong, thin, 0.05 mm, insulative layer between the components and holds the adjacent electrically conductive layers.

A reflector 121 comprising a third layer of perforated copper sheet (0.05 mm), nickel flashed, and gold plated is bonded to the upper surface of the negative plate 162, in the same manner and method as previously described. The reflector 121 provides an electrical path to the grounded, shield circuit of the LED array driver. The reflector 121 provides mechanical protection for the small wires 163 and the wire bonds conducting current between the negative plate 162 and the electrical contact lead on the top surface of each of the LED's 92. The reflector 121 provides parabolic light directing surfaces around each of the LED's to improve the efficiency for the delivery of treatment light from each LED to adjacent target tissue. As described earlier, the parabolic perforations are chemically etched into the surface of the reflector plate 121 each of the perforations forming a circular opening in the lower surface of the reflector 121 which opening is centered on a LED mounted onto the support substrate 161. The perforations 124 appear as circular holes through the reflector, each centered at a LED location. The diameter of the circular opening formed by the perforation in the lower surface is sufficient to accommodate a LED therewithin.

The cathodic conductor 163 is preferably a length of gold wire bonded at one end to the top (cathode) of a LED and the other end bonded to a specific location on the negative plate. The wire 163 completes the electrical circuit from the anode 161 at the base of each LED, across the semiconductor junction of the LED out the top cathode of the LED to the cathode layer 162. When the anode and cathode of a power supply is attached to the anodic support 161 and cathode 162 of the lights source 12, the LED's 92 will produce light.

As discussed previously, LED's generate heat as they produce light. The heat is conducted to the support 161 of the LED array and then away from the semiconductor junction within the LED 92. To remove this heat, heat transfer devices 173 or 174 are attached to the lower surface of the support 161. In the preferred embodiment of the LED array light source, all of the electrically conducting components are high thermal transfer material such as copper. The primary heat transfer component is the heat-sinked support 161. While the other components in the light source do not need to be copper, the support 161 must be made a of material which will quickly remove the heat generated by conducting the heat to a heat sink. That is to say, not all light delivery applications will generate the magnitude of heat that the present device has been subjected to. To remove the heat from the LED array during operation, a number of options are available. For example: a fluid circulating coil of tubing can be mounted to the rear of the substrate with silver or lead solder. Circulating a temperature regulated fluid through the tubing will keep the support substrate 161 temperature constant. Thermoelectric modules may also be directly attached to the support substrate. And more conventionally, finned heat sinks such as shown at 173 mounted in thermal contact with the rear surface of the support substrate will dissipate heat to the air surrounding the LED array light source. Mounting the device upon the surface of a larger structure, such as when a tail light is mounted to the metallic body of an automobile, can also provide the required heat dissipation for high current operation.

The foregoing preferred embodiment of the LED light source adapted for photodynamic therapy provides a low cost, high power excitation source for PDT which can be produced in a variety of shapes for use in a wide variety of applications. This LED array light source presented herein will allow PDT to become viable treatment modality for many more cancer patients inasmuch as it will now be cost effective for availability in the physician's office or small clinic.

The construction presented above permits high optical power output capability for the source. This capability is attributed to, inter allia; the copper materials which conduct heat from the LED's to the heat removing device affixed thereto and in thermal contact wherewith as well as the configuration of the parts including the reflector array and the reflective coatings applied thereto. The maximum current level to a LED will be limited by the difference in operating temperature between the LED electrical/optical junction and the heat dissipating base of the LED. This temperature difference is the temperature gradient of the LED. The support 161 material of the array light source does not substantially increase in temperature when the LED array is energized and operated because the large heat capacity and thermal conductivity of the copper sheet 161 does not permit a substantial temperature gradient to exist between the LED array and the fluid coolant heat sink as would a material which cannot conduct the heat away from the LED as quickly. Prior art LED display technology commonly employs a ceramic substrate which is a poor thermal conductor and adds to the thermal gradient of the LED, thus reducing the maximum current capacity of the LED array light source. The reflective surfaces of the source improve the therapeutic efficiency of the output of the array by directing LED-derived photons, which are normally absorbed by the mounting structures, to the target tissue.

The LED array light source, constructed as described herein, is rugged and exhibits extremely low electronic resistance and high current capability. The electrical circuit includes a solid copper sheet which has an electrical resistance far lower than the printed circuit board trace techniques used in display technology today and is significantly thicker. This low resistance increases the uniformity of illuminating light and overall efficiency of optical power delivery to a tissue from the LED array light source. The multilayer laminar construction can withstand both compression and G-forces without failure. The components comprising the anodic and cathodic electrical power busses 161 and 162 are mechanically much stronger than IC circuit board traces normally found supporting LED arrays. Bending and distortion of ceramic support substrates will result in cracking and/or broken components and traces. The copper construction of the present device is malleable and can be distorted to the point of permanent bends without breaking or cracking. The conductors delivering current to each LED can flex and move because they are preferably soft gold or aluminum wire, and occupy a free space which permits the wire to bend upon distortion of the substrate. The light source construction includes a unitary reflector array having small parabolic pits within the structure which provides protection for the small delicate LED wires and prevent damage with handling.

In addition to the foregoing advantages offered by the construction of the embodiment of a LED array light source described above, the method presented for manufacturing the device is simplified. The 0.025 mm thick, non-conductive adhesive layer printed on the upper surface of the support plate 161 and cured followed by the deposition of a 0.025 mm non-conductive layer of adhesive printed in a corresponding mating location on the lower surface of the cathodic sheet 162 creates a fast economical method of attaching and insulating the adjacent layers. Utilizing chemical etching, the structural components of the LED light source can be designed so as to be formed from large sheets of copper. Multiple arrays of perforations can be etched into a single copper sheet that has features for alignment. Such sheets allow the printing, stacking and bonding of the layers in the manner as described above for multiple arrays. Since the perforations in the reflector and cathodic layer permit LED's to be mounted upon the support plate after assembly, the entire light source can be constructed before any of the LED's are mounted. Thus, the LED mounting and support unit can be built and tested before expensive LED's are mounted during the manufacturing process. Mounting LED's at the end of the manufacturing cycle will reduce the cost of production due to rejects. Different colors of LED's can be mounted on the exact same sub-assembly, at the end of the manufacturing cycle, thus increasing the flexibility of the product offered and reducing the time to deliver alternate products.

Array construction has typically been orientated around printed circuit board technology. The present construction avoids the limitation inherent in prior art circuit board construction. The device can be manufactured by punching holes in continuous strips of copper sheet stock and combining the strips into a laminate with adhesive. A continuous LED mounting strips can be formed which can be populated with LED's. The LED mounting can be built into the continuous production line post-substructure assembly.

In summary, an LED array can be configured to provide power and wavelength outputs suitable for PDT. In order to achieve the required power levels, it is presently necessary to over-drive the LED's. The additional current required for over-driving generates heat at the diode junction which results in: (a) a red-shift and broadening of the output light; and (b) a shorter lifetime. To overcome these problems, the LED array is mounted on and in thermal connection with the plan surface of a heat conducting support, the support being heat-sinked thereby enabling the LED array to be cooled to control the bandwidth and wavelength of the output light and increase the lifetime of the LED array. In practice, the output wavelength depends on the diode's junction temperature. Monitoring the LED output wavelength permits adjustment of the coolant temperature and flow rate through the heat conducting support as required to maintain the junction at the desired temperature.

While particular embodiments of the present invention have been illustrated and described, it would be obvious to those skilled in the art that various other changes and modifications can be made without departing from the spirit and scope of this invention. For example, it is possible, and even desirable to mold the reflective device of the present invention from an elastomer so that the surface can be readily distorted while regaining the parabolic shape of the cups. Such a reflector would be useful for anatomically conforming applications. Single LED chips may be fabricated into an array by depositing them directly onto a chilled substrate by techniques currently used in hybrid circuit fabrication. It is therefore intended to cover in the appended claims all such changes and modifications that are within the scope of this invention.

What we claim is:

1. A light delivery device for delivering phototherapeutic light to uniformly illuminate a surface of a tissue, said device comprising: (a) a semiconductor light source producing therapeutic light; and (b) a handpiece adapted to be electrically connected to a source of electrical power, said semiconductor light source having means adapted for releasably attaching said semiconductor light source to said handpiece, said semiconductor light source further comprising, in combination:

(i) a support comprising a sheet of electrically and thermally conductive material and having a planar upper surface;

(ii) a plurality of light emitting diodes disposed in two-dimensional array upon a said planar surface of said support, each of said light emitting diodes having a first electrical connector electrical connected to said support and a second electrical connector;

(iii) a cooling means in thermal connection with said support adapted to remove heat from said support;

(iv) a cathode comprising a single sheet of electrically conductive material having a top surface and a bottom surface and a plurality of perforations therebetween, said bottom surface of said single sheet being affixed to said planar surface of said support by an electrically non-conductive adhesive, said perforations disposed on said single sheet to form a second two-dimensional ray thereon, said perforations having a large circular opening at said top surface and a small circular opening on said bottom surface of said single sheet and an inner surface therebetween and wherein each of said small circular openings circumscribe one of said light emitting diodes, and wherein the center of said small circular opening of each perforation of said plurality of parabolic perforations overlies the center of a circumscribed light emitting diode comprising said light emitting diode array.

2. The light delivery device of claim 1 wherein said inner surface of said parabolic perforations comprise a reflective material.

3. The light delivery device of claim 1 wherein said first electrical connector is in electrical communication with said support and wherein said second electrical connector is in electrical communication with said cathode.

4. The light delivery device in accordance with claim 1 further comprising a source of electrical power having an anodic output and a cathodic output wherein the anodic output is in electrical communication with said support and wherein said cathodic is in electrical communication with said cathode.

5. The light delivery device in accordance with claim 1 further comprising a reflector affixed to said upper surface of said single sheet, said reflector comprising a sheet a plurality of parabolic perforations therein, each of said parabolic perforations presenting a circular opening circumscribing and centered upon of the light emitting diodes comprising the light delivery device.

6. The light delivery device in accordance with claim 2 wherein said second electrical connector is in electrical communication with said cathode.

* * * * *